United States Patent [19]

Boesten

[11] 4,094,904

[45] * June 13, 1978

[54] PROCESS OF RACEMIZING AN OPTICALLY ACTIVE PHENYL GLYCINE AMIDE WITH OR WITHOUT A SUBSTITUTED PHENYL GROUP

[75] Inventor: Wilhelmus H. J. Boesten, Sittard, Netherlands

[73] Assignee: Stamicarbon, B.V., Geleen, Netherlands

[*] Notice: The portion of the term of this patent subsequent to July 19, 1994, has been disclaimed.

[21] Appl. No.: 748,398

[22] Filed: Dec. 8, 1976

[30] Foreign Application Priority Data

Dec. 9, 1975 Netherlands ............. 7514301

[51] Int. Cl.$^2$ ........................................... C07C 103/28
[52] U.S. Cl. ............................ 260/558 A; 260/559 A
[58] Field of Search ............ 260/558 A, 570.6, 584 R, 260/DIG. 7, DIG. 8, 559 A

[56] References Cited

U.S. PATENT DOCUMENTS

| 2,790,001 | 4/1957 | Purvio | 260/DIG. 8 |
| 3,705,900 | 12/1972 | Ryan | 260/DIG. 8 |
| 4,036,852 | 7/1977 | Boesten | 260/558 A X |

OTHER PUBLICATIONS

Chibata et al., CA 83:10843e (1975).
Sakieki et al., CA 55:3449b (1961).
Hori et al., CA 52:2056c (1958).
Betti et al., Ber., 41, pp. 2071–2073 (1908).
Suzuki et al., CA 80:133826x (1974).
Watanabe et al., CA 80:27470s (1974).
Sato et al., CA 73:120879x (1970).
Gunter et al., CA 55:14317a (1961).

*Primary Examiner*—Daniel E. Wyman
*Assistant Examiner*—Thomas A. Waltz
*Attorney, Agent, or Firm*—Cushman, Darby & Cushman

[57] ABSTRACT

The invention is directed to a process for the racemization of optically active phenyl glycine amide with or without a substituted phenyl group by heating the optically active phenyl glycine amide in a solvent in the presence of a ketone and of an acid having a dissociation constant below $1.8 \times 10^{-4}$.

7 Claims, No Drawings

PROCESS OF RACEMIZING AN OPTICALLY ACTIVE PHENYL GLYCINE AMIDE WITH OR WITHOUT A SUBSTITUTED PHENYL GROUP

BACKGROUND OF THE INVENTION

The resolution of a mixture of D- and L-phenyl glycine amide by means of an optically active acid is described in my co-pending U.S. patent applications Ser. No. 623,928, filed Oct. 20, 1975, and now U.S. Pat. No. 4,036,852 and Ser. No. 733,851, filed Oct. 19, 1976. An improved process for the resolution of a mixture of D- and L-phenyl glycine amide by means of an optically active acid is described in my co-pending U.S. patent application Ser. No. 748,399 filed concurrently herewith. The entire specification and claims of each of these three patent applications is incorporated by reference in the present specification.

The invention relates to a process of racemizing an optically active phenyl glycine amide with or without a substituted phenyl group. The phenyl group may be substituted by a substituent such as a hydroxy, halogen, nitro, or amino group. These substituted optically active phenyl glycine amides can be prepared from the corresponding amino acid by esterification followed by aminolysis of the ester with ammonia as described in the Journal of the American Chemical Soc. vol. 71 (1949) page 78, 79.

If desired, the racemized amide can be hydrolyzed to yield the corresponding amino acid again. Phenyl glycine amide can be hydrolyzed in a simple manner to form phenyl glycine, for example, by treatment with sulfuric acid, as described in the *Journal of the Chemical Society*, pages 393–397 (1966).

In the preparation of an optically active phenyl glycine amide from a mixture of D- and L-phenyl glycine amide, both antipodes of the racemate are produced. If unequal amounts of the antipodes are desired, the undesired antipode can be racemized and the resulting racemate subjected to further resolution. As used in the present specification, "a mixture of L- and D-phenyl glycine amide" means either a racemate of phenyl glycine amide, or mixtures of the racemate with either L-phenyl glycine amide or D-phenyl glycine amide.

The optically active phenyl glycines which can be easily obtained from the resolved optically active phenyl glycine amides are valuable compounds. For example, D-phenyl glycine is employed as a starting material for the preparation of α-amino benzyl penicillin. L-phenyl glycine provides a starting material for the sweetening agent L-asparagin-L-phenyl glycine alkyl ester.

SUMMARY OF THE INVENTION

According to the invention, a process has been discovered comprising racemizing an optically active phenyl glycine amide, the phenyl group of which may be substituted, in an accelerated manner. It has been found that the racemization of a optically active phenyl glycine amide can be desirably conducted by heating the optically active phenyl glycine amide to be racemized in a solvent in the presence of a ketone and of an acid having a dissociation constant below $1.8 \times 10^{-4}$. As used in the present application, it is to be understood that "an optically active phenyl glycine amide" includes both unsubstituted optically active phenyl glycine amide and optically active phenyl glycine amide in which the phenyl group is substituted with, for example, a hydroxy, halogen, nitro or amino group.

It is therefore an object of the present invention to racemize an optically active phenyl glycine amide in an accelerated manner.

Surprising, it has been found that the object of the present invention can be realized by racemizing an optically active phenyl glycine amide in the presence of a ketone and of an acid having a dissociation constant below $1.8 \times 10^{-4}$.

DETAILED DESCRIPTION OF THE INVENTION

The invention is directed to a process of racemizing an optically active phenyl glycine amide, the phenyl group of which may be substituted, in a solvent in the presence of a ketone and of an acid having a dissociation constant below $1.8 \times 10^{-4}$.

Suitable acids are, for example, formic acid and acetic acid. In addition, use may be made of optically active acids e.g. optically active pyrrolidone-5-carboxylic acid and optically active N-acetyl phenyl glycine. These optically active acids are also suitable for the optical resolution of mixtures of D- and L-phenyl glycine amide, as described in my co-pending applications incorporated herein by reference.

In the process of the present invention, preferably a quantity of acid is used which is equivalent to the quantity of phenyl glycine amide. An amount less than an equivalent amount, e.g. half the equivalent amount, of acid can also be used, but in that case undesirable side reactions may occur. A quantity of acid which is in excess of the equivalent of the phenyl glycine amide present may also be used, although there is no particular advantage in using excess acid.

The racemizing process of the present invention is preferably effected at a temperature between about 35° and about 150° C. It is preferred to effect the racemizing process of the present invention at a temperature between about 50° and about 100° C.

The ketone used in the racemizing process of the present invention may be selected from the group consisting of acetone, methyl ethyl ketone, pentanone, cyclohexanone, and mixtures thereof. It is believed that other ketones will also be operative in the process of the present invention.

The amount of ketone used in the process of the present invention may be varied within wide limits. It has been found that a small quantity of ketone, for example 0.1 mole of ketone per mole of phenyl glycine amide is effective in the process of the present invention. Of course, larger amounts of ketone may also be used. If the amount of ketone used is sufficiently large, the ketone can also serve as a solvent for the racemizing mixture. However, it is also contemplated in the process of the present invention that other solvents may be used. For example, water, an alcohol, benzene, toluene, chloroform, and ethyl acetate may also be used as solvents.

The process of the present invention will be further illustrated by the following examples, which are intended to be illustrative only and are meant to include all techniques equivalent thereto.

EXAMPLES

EXAMPLE I

In a flask equipped with a stirrer and a reflux cooler a solution of 1.5 g (0.01 gmole) L-phenyl glycine amide and 0.6 ml (0.01 gmole) acetic acid in 20 ml water and 80 ml acetone is boiled for 24 hours (58° C), with stirring and reflux.

After cooling to 20° C, the rotation of this solution is determined. It is $[\alpha]_D 20 = 0.3°$ The rotation of the original solution is:

$[\alpha]_D 20 = 5.1°$.

Comparison of these rotation values shows (50 − 50 × 0,3/5,1) × 2 = 94% of the L-phenyl glycine amide to have been racemized.

EXAMPLE II

In a flask equipped with a stirrer and a reflux cooler a solution of 1.5 g (0.01 gmole) L-phenyl glycine amide, 0.4 ml (0.011 gmole) formic acid in 50 ml methyl ethyl ketone and 10 ml water is boiled with reflux for 20 hours (80° C).

After cooling to 20° C, the rotation of this solution is $[\alpha]_D 20 = +0.9°$.

The rotation of the original solution is $[\alpha]_D 20 = +7.7°$.

Comparison of the rotation values shows 88% of the L-phenyl glycine amide to have been racemized.

EXAMPLE III

In a flask equipped with a stirrer and a reflux cooler 1.5 g (0.01 gmole) L-phenyl glycine amide and 0.6 ml (0.01 gmole) acetic acid in a mixture of 50 ml methanol and 0.45 ml (0.005 gmole) methyl ethyl ketone is boiled with reflux for 6 hours at 60° C.

After cooling to 20° C the rotation of the resulting solution is measured. It is $[\alpha]_D 20 = 5.05°$ The rotation of the original solution is $[\alpha]_D 20 = 8.90°$ Comparison of the rotation values shows 44% of the L-phenyl glycine amide to have been racemized.

EXAMPLE FOR COMPARISON

Example III is repeated, this time without addition of methyl ethyl ketone.

After 6 hours' boiling, the rotation of the solution is $[\alpha]_D 20 = 8.40°$.

Comparison of the rotation values shows only 6% of the L-phenyl glycine amide to have been racemized.

EXAMPLE IV

In a flask equipped with a stirrer and a reflux cooler 4.5 g L-phenyl glycine amide and 3.9 g D-2-pyrrolidone-5-carboxylic acid in 200 ml methanol and 10 ml acetone is heated at boiling temperature for 25 hours whilst being stirred.

After cooling to 20° C, 3 ml concentrated hydrochloric acid (35%-wt.) is added. Next, the reaction mixture is concentrated in vacuo (12 mm Hg) at 30° C to a volume of 40 ml. The DL-phenyl glycine amide.HCl formed in this way is recovered on a filter and washed on this filter with 5 ml $[\alpha]_D 20 = +0.4°$ (c = 0.8; water)

In Beilstein 14, III, p. 1189. the specific rotation of L-phenyl glycine amide. HCl is given as $[\alpha]_D 20 = +100.8°$ (c = 0.8; water).

Comparison of the rotation values shows 99,5% of the L-phenylglycine amide to have been racemized.

Thus it is apparent that there has been provided in accordance with the invention, a process for the racemization of optically active phenyl glycine amide that fully satisfies the objects, aims, and advantages set forth above. While the invention has been described in conjunction with specific embodiments thereof, it is apparent that many alternatives, modifications, and variations will be evident to those skilled in the art in light of the foregoing description. Accordingly, it is intended to embrace all such alternatives, modifications, and variations as fall within the spirit and broad scope of the following claims. methanol. After drying, the resulting salt weighs 4.4 g. The specific rotation of this salt is

What is claimed is:

1. A process for racemizing an optically active form of phenyl glycine amide, consisting essentially of:
   mixing an optically active form of phenyl glycine amide, a solvent for said phenyl glycine amide, a ketone, selected from the class of acetone, methylethyl ketone, pentanone, cyclohexanone, and mixtures thereof, and an acid having a dissociation constant below $1.8 \times 10^{-4}$, said ketone being present in an amount of at least 0.1 mole of ketone per mole of phenyl glycine amide; and
   heating said mixture to a temperature between 30° and 150° C.

2. The process according to claim 1, wherein said mixture is heated to a temperature between 50° and 100° C.

3. The process according to claim 1, wherein said acid is present in an amount equivalent to the phenyl glycine amide present.

4. The process according to claim 1, wherein said acid is selected from the group consisting of formic acid, acetic acid, and mixtures thereof.

5. The process according to claim 1, wherein said acid is an optically active acid.

6. The process according to claim 1, wherein said solvent is said ketone.

7. The process according to claim 1 wherein, said solvent is selected from the group consisting of water, an alcohol, benzene, toluene, chloroform, ethyl acetate, and mixtures thereof.

* * * * *

UNITED STATES PATENT AND TRADEMARK OFFICE
CERTIFICATE OF CORRECTION

PATENT NO. : 4,094,904
DATED : June 13, 1978
INVENTOR(S) : Wilhelmus H.J. BOESTEN It is certified that error appears in the above-identified patent and that said Letters Patent are hereby corrected as shown below:

At col. 4, line 8, after "ml" the following should appear:

--methanol. After drying, the resulting salt weighs 4.4 g. The specific rotation of this salt is--

At col. 4, lines 28-29, the following should be deleted:

"methanol. After drying, the resulting salt weighs 4.4 g. The specific rotation of this salt is".

Signed and Sealed this

Eighteenth Day of November 1980

[SEAL]

Attest:

SIDNEY A. DIAMOND

Attesting Officer

Commissioner of Patents and Trademarks